United States Patent
Spagnoli et al.

(10) Patent No.: US 8,357,494 B2
(45) Date of Patent: Jan. 22, 2013

(54) ANTI-CLUSTERIN OLIGOCLONAL ANTIBODIES FOR DIAGNOSIS AND PREDICTION OF THE AGGRESSIVENESS OF TUMOURS, DIAGNOSTIC METHOD AND RELATED KITS

(75) Inventors: Luigi Giusto Spagnoli, Nerola (IT); Sabina Pucci, Rome (IT); Elena Bonanno, Rome (IT); Flavia Pichiorri, Rome (IT); Gennaro Citro, Rome (IT)

(73) Assignees: Universita' Delgi Studi "Tor Vergate", Rome (IT); Institute Fisioterapici Ospitalieri, Rome (IT)

( * ) Notice: Subject to any disclaimer, the term of this patent is extended or adjusted under 35 U.S.C. 154(b) by 971 days.

(21) Appl. No.: 10/590,479

(22) PCT Filed: Feb. 17, 2005

(86) PCT No.: PCT/IT2005/000088
§ 371 (c)(1), (2), (4) Date: Jul. 20, 2007

(87) PCT Pub. No.: WO2005/080434
PCT Pub. Date: Sep. 1, 2005

(65) Prior Publication Data
US 2008/0317771 A1    Dec. 25, 2008

(30) Foreign Application Priority Data
Feb. 25, 2004   (IT) .............................. RM2004A0098

(51) Int. Cl.
| G01N 33/53 | (2006.01) |
| G01N 33/536 | (2006.01) |
| G01N 33/567 | (2006.01) |
| G01N 33/574 | (2006.01) |
| C07K 1/04 | (2006.01) |
| C07K 7/08 | (2006.01) |
| C07K 9/00 | (2006.01) |
| C07K 14/435 | (2006.01) |
| A61K 38/10 | (2006.01) |
| A61K 38/18 | (2006.01) |
| A61K 39/385 | (2006.01) |
| A61K 39/395 | (2006.01) |

(52) U.S. Cl. ........ 435/7.1; 435/7.5; 435/7.91; 435/7.92; 435/21; 435/28; 435/40.52; 436/64; 436/503; 436/542; 436/547; 436/811; 530/387.7; 530/387.9; 530/389.1; 530/389.7; 530/391.1

(58) Field of Classification Search .................. None
See application file for complete search history.

(56) References Cited

U.S. PATENT DOCUMENTS
5,663,315 A * 9/1997 Scheele et al. ............... 536/23.5

FOREIGN PATENT DOCUMENTS
WO   03/086326 A3   10/2003
WO   WO03/086326   *   3/2006

OTHER PUBLICATIONS

Kerr and Thorpe (Immunochemistry LabFax, 1994, pp. 118, 128-129, 158).*
Danik et al (PNAS, 1991, vol. 88, pp. 8577-8581).*
Kapron et al (Protein Science, 1997, vol. 6, pp. 2120-2133).*
Maloy and Coligan ('Selection of Immunogenic Peptides for antisera Production', In: Current Protocols in Immunology, 1991, pp. 9.3.1-9.3.5).*
Wong et al (European Journal of Biochemistry, 1994, vol. 221, pp. 917-925).*
Yang et al (Proceedings of the National Academy of Science, 2000, vol. 97, pp. 5907-5912).*
O'Sullivan et al (Cell Death and Differentiation, 2003, vol. 10, pp. 914-927).*
Kerr and Thorpe (Immunochemistry LabFax, 1994, pp. 118, 134-135, 142-143, 158-161).*
Johnathan Lakins et al., "Clusterin Biogenesis Is Altered during Apoptosis in the Regressing Rat Ventral Prostate", The Journal of Biological Chemistry, vol. 273, No. 43, Oct. 23, 1998, pp. 27887-27895, XP002329183, ISSN: 0021-9258.
Axel Wellmann et al., "Detection of differentially expressed genes in lymphomas using cDNA arrays: Identification of clusterin as a new diagnostic marker for anaplastic large-cell lymphomas", Bood, vol. 96, No. 2., Jul. 15, 2000, pp. 398-404, XP002222896, ISSN: 0006-4971.
Maximino Redondo et al., "Overexpression of Clusterin in Human Breast Carcinoma", American Journal of Pathology, vol. 157, No. 2, Aug. 2000, pp. 393-399, XP001206323, ISSN: 0002-9440.
Min-Jue Xie et al., "Expression of Clusterin in Human Pancreatic Cancer", Pancreas, vol. 25, No. 3, Oct. 2002, pp. 234-238, xp009047969, ISSN: 0885-3177.
Maurizio Scaltriti et al., "Clusterin (SGP-2, ApoJ) Expression is Downregulated in Low- and High-Grade Human Prostate Cancer", International Journal of Cancer, vol. 108, No. 1, Jan. 1, 2004, pp. 23-30, XP002329184, ISSN: 0020-7136.
J O'Sullivan et al., "Alterations in the post-translational modification and intracellular trafficking of clusterin in MCF-7 cells during apoptosis" Cell Death and Differentiation, vol. 10, No. 8, XP009047977, ISSN: 1350-9047.
Sabina Pucci et al., "Modulation of different clusterin isoforms in human colon tumorigenesis", Oncogene, Mar. 25, 2004, vol. 23, No. 13, pp. 2298-2304, XP002329185, ISSN: 0950-9232.

* cited by examiner

*Primary Examiner* — Karen Canella
(74) *Attorney, Agent, or Firm* — Arent Fox LLP

(57) ABSTRACT

The invention concerns anti-clusterin oligoclonal antibodies able to recognize and bind in a selective and specific way antigenic epitopes of clusterin isoforms to be used in tumors diagnosis and in the prediction of their malignancy grade, diagnostic method and related kits.

17 Claims, 2 Drawing Sheets

T → Tumoral Tisue
S → Healthy Tissue

ANTI-CLUSTERIN OLIGOCLONAL ANTIBODIES FOR DIAGNOSIS AND PREDICTION OF THE AGGRESSIVENESS OF TUMOURS, DIAGNOSTIC METHOD AND RELATED KITS

CROSS-REFERENCE TO RELATED APPLICATION

This application is a National Stage entry of International Application No. PCT/IT2005/000088, filed Feb. 17, 2005, the entire specification claims and drawings of which are incorporated herewith by reference.

SEQUENCE LISTING

The instant application contains a Sequence Listing which has been submitted in ASCII format via EFS-Web and is hereby incorporated by reference in its entirety. Said ASCII copy, created on Nov. 17, 2010, is named 02607307.txt and is 2,105 bytes in size.

This invention concerns anti-clusterin oligoclonal antibodies for tumour diagnosis and prediction of the malignancy grade of the tumour, diagnostic method and related kits.

In particular, the invention concerns anti-clusterin oligoclonal antibodies selective and specific for diagnosis of the onset or the relapse and the prediction of aggressiveness of tumours such as colon, breast, prostate, testis and ovary carcinomas, tumours of the central nervous system (SNC) and of the haemo-lymphopoietic system.

At present, colon cancer is second only to lung cancer in men and to breast carcinoma in women, for incidence and mortality in western countries.

In Italy, the incidence of colon cancer is: 40 new cases every 100,000 inhabitants (30,000 new cases per year). The mortality is 18,000 cases per year.

The higher incidence per age is observed between the sixth and seventieth decade, while 60% of the patients survive up to five years. The most important reason for the low percentage of recoveries is due to the fact that when the primary tumour is removed, a high number of patients have already developed micro-metastases, principally at liver. Therefore, methods for early screening are requested. At present, the early diagnosis protocols (secondary prevention) consist of rectal exploration, determination of fecal occult blood, recto-sigmoidoscopy or pan-colonoscopy, periodically performed on individuals of 45 years of age and older and non-symptomatic. Periodic pan-colonoscopy is the only procedure for early diagnosis of neoplasia, on individuals that are part of the so called "at risk population", that is individuals with positive familiar anamnesis for colorectal cancer, patients with already a neoplasia or affected by syndrome with an high risk of neoplasia insurgence. Obtaining more information on the molecular alterations of a tumour would help to subdivide patients affected by the same tumour in groups with different prognosis, and then perform the specific therapeutic protocols. Moreover, this molecular alteration could be the target of a specific therapy that would revolutionize the pharmacological therapy of cancer.

Recent studies have demonstrated an increase in clusterin expression in breast carcinoma (Redondo et al, 2000), suggesting a possible role of this protein in tumour progression.

Clusterin is an eterodimeric ($\alpha$ and $\beta$ chains) ubiquitous glycoprotein implicated in a large number of physiological processes and in the control of cellular proliferation (Murphy et al, 1988; Aronow et al, 1993; Fratelli et al, 1996; Ho et al, 1998; Humphreys et al, 1999; O'Sullivan et al, 2003; Zhou et al, 2002; Bettuzzi et al, 2002). A number of isoforms have been characterized that differ in the grade of glycosilation and in their function.

The authors of the present invention have studied clusterin expression (Pucci et al, 2004) in order to elucidate its role in tumour progression, in particular in the adenoma-carcinoma sequence of colorectal cancer, a well known human tumour model. In this context, the observation of 35 samples of human intestinal mucosa, such as endoscopic biopsies and surgical specimens has shown a different modulation of clusterin isoforms in the various cell compartments, directly related to tumour progression. In fact, in healthy colon mucosa it has been observed clusterin with an exclusive nuclear localization, that regulates cell cycle progression and apoptosis induction. On the other hand, in carcinogenesis and in tumour progression a clear increase in the cytoplasmic isoform expression has been observed, while the nuclear isoform is lacking.

Evidences about the protein localization have helped recognize two principal isoforms: a nuclear non-glycosylated isoform in healthy mucosa and in adenomas; a cytoplasmic glycosylated isoform highly expressed in neoplastic cells and absent in healthy mucosa. The results concerning the modulation of different clusterin isoforms in the tumourigenesis of colorectal cancer shed light on the controversial data on increase of clusterin in tumours and on the role of the protein in apoptosis induction, suggesting a possible role of clusterin as a potential new marker for the diagnosis and prognosis of colorectal cancer.

The use of clusterin as a diagnostic marker in some pathological conditions such as diabetes mellitus of type II and some coronary pathologies has already been described in the Greek patent GR 20020100196. The Greek document describes an ELISA method which uses two commercial antibodies (one of which is conjugated with the HRP enzyme), for the quantitative determination of serum ApoJ/Clusterin levels, related to the above mentioned pathologies.

There was just one previous attempt to determine ApoJ by ELISA in tumoural pathologies, specifically in the blood of prostate carcinoma patients (Morrisey et al, 2001), as referred in the Greek document.

On the basis of the above, it is clear the need of new materials and methods for diagnosis and prediction of the grading and clinical staging of some tumours i.e. colorectal cancer, that would overcome the restrictions of the invasive methods used at present.

The authors of this invention have highlighted that the appearance and the progressive increase of the clusterin cytoplasmic isoform in tumours correlates to a significant increase of clusterin in the serum of patients affected by tumoural pathologies and in particular by colorectal cancer. On the basis of this observation, the authors have tested a new method of immuno-dosage of clusterin with the use of antibodies that can recognize specifically and selectively the cytoplasmic and nuclear isoforms of clusterin, for diagnosis of the molecular alterations that could define a prognosis and give therapeutic indications.

In fact, as already described the disappearance of clusterin nuclear non-glycosylated isoform and the preferential expression of a second isoform completely glycosylated and cytoplasmic seems to be directly related to the aggressiveness of the tumour and to its metastatic potential (Pucci et al, 2004).

In particular, this dosage method of the two clusterin isoforms, using antibodies according to the present invention, not only represents a non invasive tool, but it is also an easy and not expensive approach for the patient's follow-up and it could help formulate a "biological aggressiveness index" of the neoplasia, that would help standardizing this method. In particular, the authors have tested a standard curve, where the protein of reference is not the purified clusterin but a peptide synthesized on the basis of the new epitope chosen for immunization.

Serological techniques such as ELISA and/or immunofluorescence used presently need monoclonal antibodies, because of the difficulty in obtaining specific sera.

The authors of this invention have now obtained sera containing oligoclonal antibodies specific and selective for the selected epitopes, belonging to clusterin cytoplasmic and nuclear isoforms. These oligoclonal antibodies have not the disadvantages of reproducibility, production costs and conservation of monoclonal antibodies obtained from hybridomas. Indeed, selection and conservation of an hybridoma has a number of limitations: low reproducibility of the clone and antibody specificity toward the epitope, technical difficulty in the production of the hybridoma, high cost for the maintenance and difficult conservation of samples in time. Moreover, the manufacturing of oligoclonal antibodies based on the selection of very short antigenic epitopes (synthesized on solid phase) permits the determination of a small repertoire of antibodies that are comparable to monoclonal antibodies, considering the characteristics of specificity and affinity. According to this invention and for an easier application of the oligoclonal antibodies, the antigenic sequences of the epitopes have been chosen among the most highly conserved both in human and mouse, permitting a wider application for animal model research. Moreover, this choice allows to minimize the binding with human proteins different from clusterin. The selection of these epitopes has also been made to guarantee the maximum specificity and efficiency and the minimum cross-reactivity of the oligoclonal antibody with the various glycosylated isoforms of cytoplasmic clusterin and to obtain highly specific and selective antibodies for the non-glycosylated nuclear isoform. It must be pointed out that the commercial anti-clusterin antibodies are not able to identify this nuclear isoforms, because the immunization used for their preparation is done administering the proteins purified from serum, that the authors have recently demonstrated it contains exclusively the glycosylated isoform of the protein. The authors of the present invention have previously found that in the colorectal cancer the secreted isoform of cytoplasmic clusterin is released in the extra-cellular space and in the lumen of colon, thus an increased level of clusterin also in the stools of the colon carcinoma patients could be expected. Therefore, the dosage of clusterin can be carried out, further than that in peripheral blood, also in the stools of the colorectal cancer patients with a blood-stool cross-shaped test, highly specific for the colon carcinoma. In this manner, the problem of the interference of the increased level of clusterin due to other not tumoural or tumoural diseases (cancer of breast, prostate, testicle, ovary, SNC, haemo-lymphopoietic system) is abolished.

Therefore, it is an object of the present invention oligoclonal antibodies which are able to recognize and to bind in a specific and selective manner the antigenic epitope of at least one isoform of the clusterin, said antigenic epitope being characterised by a length comprised between 10 and 20 amminoacidic residues. The clusterin isoform which is recognized by the anti-clusterin oligoclonal antibodies can be the not-glycosylated nuclear or the glycosylated cytoplasmic one. According to the present invention, these oligoclonal antibodies discriminate between different clusterin isoforms. In particular, the antigenic epitope selected to produce the oligoclonal antibodies against the nuclear not-glycosylated clusterin isoform comprises an amminoacidic sequence selected from the group consisting of:

| QFNWVSRLANTQGEDQK; | (SEQ ID No. 1) |
| TKLKELPGVCNETMMALWEE; | (SEQ ID No. 2) | and derivatives thereof obtained by deletion, substitution or addition of one or more amminoacids, which maintain the same immunogenic property of the original epitope. The antigenic epitope chosen to produce the oligoclonal antibodies directed against the cytoplasmic glycosylated isoform can comprise one of the following amminoacidic sequences:

| TKLKELPGVCNETMMALWEE; | (SEQ ID No. 2) |
| TNEERKTLLSNLEEAK; | (SEQ ID No. 3) |
| METVAEKALQEYRKK; | (SEQ ID No. 4) | and their derivatives obtained by the means of deletion, substitution either addition of one or more amminoacids that maintain the same immunogenic property of the original epitope.

According to the present invention, the oligoclonal antibodies can be tagged preferably with a fluoro-chrome, a radioactive isotope, an enzyme, biotin or a chemiluminescent substance. The fluoro-chrome being the fluorescein or phycoeritrin, or rodamine, or the texas red, or cumarin; the enzyme being the peroxidase of radish (HRP) or alkaline phosphatase; the radioactive isotope could be $^{14}$C, or $^{3}$H; the chemi-luminescent substance can be luciferin.

They constitute further subjects of the present invention antigenic epitopes belonging to at least one of the clusterin isoforms, cytoplasmic and/or nuclear, comprising at least one of the following amminoacidic sequences:

| QFNWVSRLANLTQGEDQK; | (SEQ ID No. 1) |
| TKLKELPGVCNETMMALWEE; | (SEQ ID No. 2) |
| TNEERKTLLSNLEEAK; | (SEQ ID No. 3) |
| METVAEKALQEYRKK; | (SEQ ID No. 4) | and their derivatives obtained by deletion, substitution or addition of one or more amminoacidic residues that maintain immunogenic properties of the original epitope.

Further issue of the present invention is represented by the method of preparation of the oligoclonal antibodies, how previously described, comprising the following phases:
a) Solid phase synthesis of at least one of the antigenic epitopes, described from above;
b) Conjugation of at least one antigenic epitope with a protein carrier as immunogen, preferably bovine serum albumin;
c) Immunization in animal with the immunogen epitope (carrier-conjugated), in complete Freund adjuvant;
d) Withdrawal of the serum from animal, preferably rabbit, and purification of the oligoclonal antibodies, e.g. by affinity chromatography.

Further issue of the present invention is an immunological assay performed to detect clusterin protein levels in biological samples for diagnosis of tumour and prediction of its malignancy grade. The immunological method comprises the following phases:
a) Extraction of the proteins from the biological sample, such as blood, stool, seminal fluid, pleural and ascitic effusions, urine, liquor;

b) Incubation in timely condition of the protein extracted with at least one of the oligoclonal antibodies above described, to form an antigen-antibody complex;

c) Qualitative and quantitative detection of this antigen-antibody complex.

In particular, the immunological method according to this invention allows the diagnosis of tumours such as colorectal, breast, prostate, testis and ovary carcinomas, tumours of the Central Nervous System and of the haemo-lymphopoietic system.

The determination in phase c) can be performed by using one of the following techniques: ELISA, Western Blot, RIA, immunohistochemistry detected with fluorochromes (immunofluorescence) or enzymatic method, or with a combination of these techniques.

This invention also includes a diagnostic kit for the diagnosis of neoplasia and for the prediction of its malignancy grade, comprising at least one of the oligoclonal antibodies above described. The tumors that can be detected are, for example, colorectal, breast, prostate, testis and ovary carcinomas, tumours of the Central Nervous System and of the haemo-lymphopoietic system. Finally, a further topic of the present invention is represented by the use of at least one of the oligoclonal antibodies described previously, for the qualitative and quantitative determination of the levels of at least one clusterin isoforms, in a biological sample such as blood, stool, seminal liquid, pleural and ascitic effusion, urine, liquor, for diagnosis of tumours (e.g. colorectal, breast, prostate, testis, ovary carcinomas, tumours of the Central Nervous System and of the haemo-lymphopoietic system) and prediction of their aggressiveness.

The qualitative or quantitative determination can be carried out by using one of the following techniques: ELISA, Western Blot, RIA, immunohistochemistry detected with fluorochromes (immunofluorescence) or enzymatic method, or with a combination of them.

To better clarify, the term "oligoclonal antibodies" means a limited repertoire of polyclonal antibodies obtained by later on cycles of specific immunization, at the conclusion of which antibodies will be obtained that are comparable to monoclonal antibodies, considering the characteristics of specificity and affinity.

The present invention will be now described to illustrate it, but not to limit it, according to the preferred embodiments, with special reference to the attached figures, in which.

Figure 3:
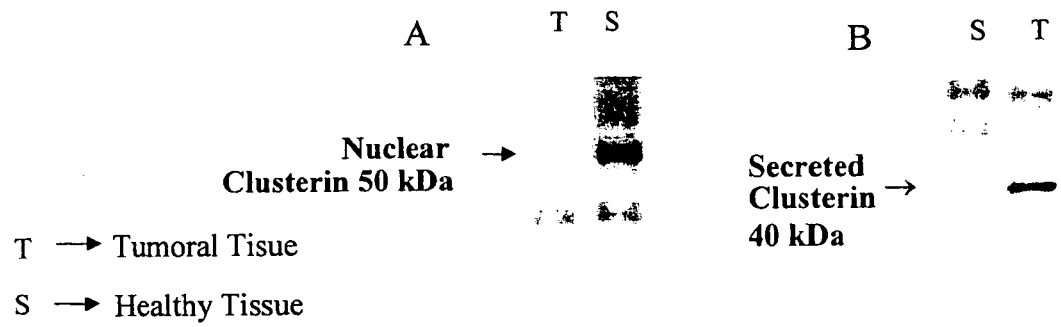

FIG. 3 shows the results obtained by ELISA, performed to analyze nuclear and secreted clusterin, in tumoural tissues and in corresponding normal samples; panel A shows the results obtained using the antibody directed against not glycosylated nuclear clusterin isoform (antigenic epitope SEQ ID No1); panel B shows the detection with antibody against the secreted glycosylated clusterin (antigenic epitope SEQ ID No4).

Figure 4:
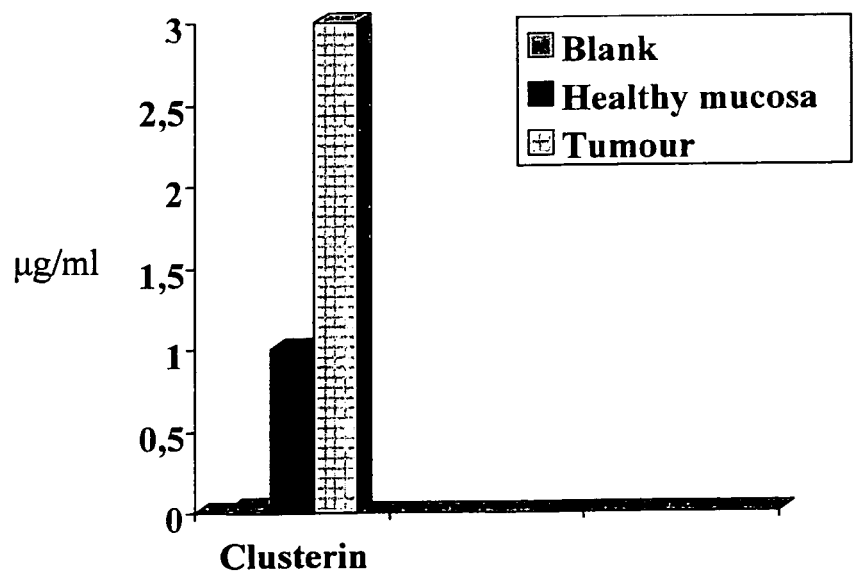

FIG. 4 shows the dosage of clusterin (μg/ml) by ELISA in the culture supernatant fraction of ex vivo-isolated tumoural cells, compared to cells from healthy colonic mucosa (number of cells seeded: $10 \times 10^7$).

EXAMPLE 1

Immunization Procedure and Anti-Clusterin Oligoclonal Antibodies Production

In order to obtain a specific anti-clusterin oligoclonal antibody the standard immunization technique has been used. The method consists on to immunize rabbit or other animal against a specific immunogenic epitope of the protein. In the serum of the immunized animal will be found polyclonal antibodies produced from different clones of activated plasmacells.

Materials and Methods:

Immunogen Production: Synthesis and Purification

Short Clusterin-specific antigenic sequences synthesized in solid phase and having a length from 10 to 20 amminoacids have been used.

A comparison between human and murine (*mus musculus*) amminoacidic sequence has been performed and the antigenic epitopes have been characterized using the algorithm of Kolaskar A. S. and Tongaonkar P. C. (1990), accessible from the program "Antigenic Peptide Prediction" (www.mifoundation.org).

The sequences, shared between man and mouse (the antibodies so can be employed in the mouse and in the rat) were chosen to contain an antigenic epitope that could be potentially glycosylated. Two likely sites of protein glycosilation allowing the discrimination between the two different isoforms (glycosylated or not glycosylated) were selected and the shorter sequence was chosen in order to obtain the greatest specify and efficiency and the smaller cross-reactivity with the different glycosylated isoforms of clusterin. In fact, the immunization performed with not glycosylated small epitopes agreed to obtain specific and selective antibodies for the recognition of the nuclear form of clusterin (not glycosylated).

The identification of the different isoforms of clusterin was obtained in Western Blot analysis by denaturing the proteins, in a protein extract from tissue. The selected amminoacidic sequences are: QFNWVSRLANLTQGEDQK (SEQ ID No 1), that consists in a not-glycosylated antigenic peptide of the α chain that recognize the nuclear form of clusterin; TKLKELPGVCNETMMALWEE (SEQ ID No 2), that consists in an not-glycosylated antigenic peptide of the β chain (used to produce the second antibody against the nuclear isoform), including the glycosilation site in the position 103 (underscored).

In order to obtain the immunogenicity, these peptides were linked to a carrier protein such as the Bovine serum albumin, (BSA), highly stable and soluble in the plasma. A commercial kit "Imject®Immunogen EDC Conjugation kit", Pierce (Rockford, Ill., US) was used.

The animal model was selected taking into account the high inter-specie homology and conservation of the protein sequence. Three epitopes were used for the rabbit immunization because of the poor immunogenicity of the antigen, despite the conjugation with BSA and administration of complete Freund adjuvant.

In particular, the following three epitopes have been used: TKLKELPGVCNETMMALWEE (SEQ ID No 2) that consists in a glycosylated antigenic peptide of the β chain used to produce the second antibody against the cytoplasmic iso-form including the glycosilation site in the position 103 (underscored); TNEERKTLLSNLEEAK (SEQ ID No 3) that consists in a peptidic sequence of the β chain used to identify the cytoplasmic form; METVAEKALQEYRKK (SEQ ID No 4) that is the antigenic peptide of the α chain, used to determine the presence of the cytoplasmic form.

The immunogenic solution constisting in carrier-linked antigenic peptide and complete Freund adjuvant was prepared in a volume of 150 μl and inoculated under-skin in rabbit. For every not-glycosylated or glycosylated peptide synthesized in solid phase, three rabbits were immunized following the protocol of the Corning Hazleton Virginia (Wien, Va.). In particular two of the peptides selected have been used solely or in combination, in a 1:1 ratio.

Moreover, an epitope of the clusterin β chain was used that did not include potentially glycosylated sites, in order to obtain an antibody able to detect all the clusterin isoforms.

The immunization with the epitopes containing potentially glycosylated sites allowed to discriminate both by Western blot and ELISA the cytoplasmic isoform of clusterin, a new marker of tumour aggressiveness and metastatic potential. After 7 days from the first immunization with the immunogenic peptides the cyclic immunization were performed ones every 7 days, for 6 times, in order to obtain an antibody repertoire with high specificity and affinity. After 3 cycles of immunization the antibody production has been analysed by ELISA, a technique used to monitor the presence of a specific antibody in the serum.

The serum was obtained from 5 ml of blood of the immunized rabbit. The control serum consisted in the pre-immune serum of the same animal withdrawn before the first immunization. The blood for the affinity and specificity test was collected after the $4^{th}$, $5^{th}$ and $6^{th}$ immunization.

After the $5^{th}$ and the $6^{th}$ immunization the antibodies from the rabbit sera were precipitated with a saturated sulphate ammonia solution and purified by affinity chromatography, using protein A bound to agarose beads (SIGMA). The rabbit IgG were obtained after a wash in acid buffer 0.05M $Na_2HPO_4$, 0.025M citric acid pH3.

Screening of the Anti-Serum Antibodies and Specificity Tests

The immune response has been evaluated by ELISA, to the beginning of the third cycle of immunisation.
Blood pulled out from three different rabbits was analysed for the evaluation of the adequacy for the ELISA test. In particular, the title of the anti-serum with different dilutions in the range of highest binding level, together with the sensitivity and the specificity of the ELISA have been examined.

After the sixth immunisation, the following tests have been performed.

For the binding assays to the different dilution ranges, the distinct antibodies were incubated in complete culture medium (control), or in medium supplemented with serum, in presence of known amounts of the peptide. The percentage of bounded peptide and the corresponding dilution of the antiserum were reported in a diagram and the antiserum dilution binding from 30% to 40% of total peptide has been calculated.

The proper dilution of the antiserum has been used to perform a standard scale as reference extending from 0.03 to 300,000 ng/ml, to evaluate the assay sensitivity.
The cross-reactivity with other known lipoproteins: Apo E, Apo Al and the immunogen transport protein (BSA), has been evaluated to the concentrations from 0.50 to 300,000 ng/ml. The percentage of cross-reactivity has been evaluated using the formula: 50% molar concentration of clusterin peptide/ concentration of other protein compound in the assay. The results are shown in Table 1.

Hence, the anti-sera at higher title and lower cross-reactivity have been chosen.
The oligoclonal antibodies selected after six cycles of immunisation have been used to analyse the expression profiles of clusterin, in protein extracts obtained from murine and human tissue biopsies. The expression analysis in whole cell lysates with protein extracts from murine and human tissues allowed us to study the protein expression both qualitatively and quantitatively.

By the Western Blotting technique, the oligoclonal antibody (1:1000 dilution) is able to recognize the nuclear clusterin/ApoJ protein, with an almost exclusive affinity for this isoform. In fact, there are revealed a 55 kDa band for the nuclear non-glycosylated protein (Burkey et al, 1991; Wong et al, 1993; Lakins et al, 1998; Leskov et al, 2003) and a 80 kDa band, which represents the non-glycosylated precursor protein (holo-protein), in human as well as in mouse. This demonstrates that the antibody does not cross-react with other proteins and therefore is highly specific.

Results

The antibodies against the SEQ ID No.1 and the SEQ ID No.2 epitopes have been tested by denaturing Western Blot for the revelation of the nuclear non-glycosylated clusterin isoform and to verify their ability to reveal the molecular weights, corresponding to the diverse clusterin isoforms, in a protein lysate.

Indeed, nuclear clusterin involved in cell proliferation regulation and apoptosis induction has been found in healthy colon mucosa. A total protein lysate from healthy colon mucosa has been prepared. The protein amount has been determined by Bradford assay, using a standard curve (BSA) and 15 μg of protein extract have been loaded on a poliacrylamide denaturing gel.

The Western Blot analysis has shown that the two antibodies for the non-glycosylated form have a high affinity for the nuclear non-glycosylated form of the protein (50-55 kDa).

Figure 1:
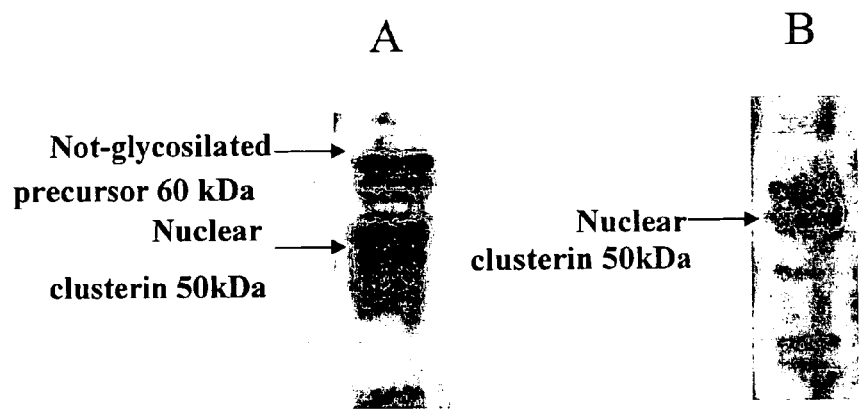
FIG. 1 shows the results obtained by Western blot analysis of the nuclear form of clusterin; in panel A, antibody against a not glycosylated antigenic epitope of the clusterin α-chain, SEQ ID No 1 has been used; in panel B the antibody has been obtained by immunization with a not glycosylated antigenic epitope of the clusterin β-chain, SEQ ID No 2.

In FIG. 1, the Western Blot for nuclear clusterin is shown. The high affinity antibodies for the non-glycosylated isoform were obtained in rabbits with a booster after 5 immunizations. "Booster" is the exponential growth phase of immunologic response induced in an animal by the antigen.

Figure 2:
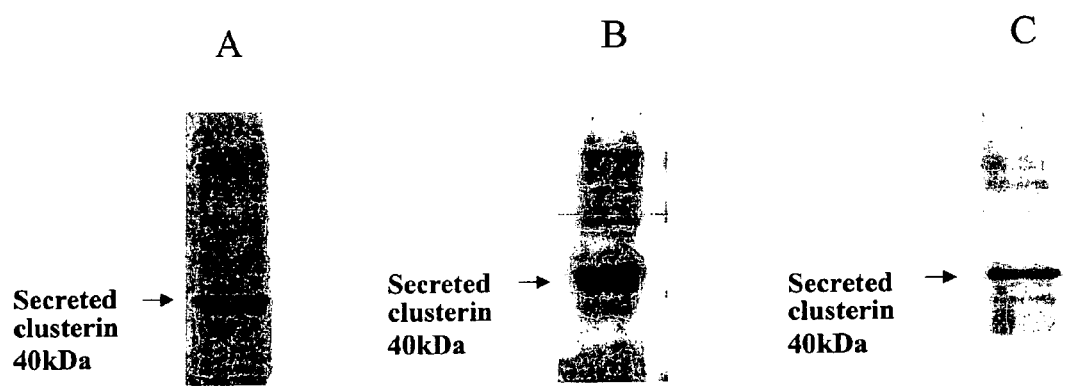
FIG. 2 shows the Western blot analysis for glycosylated cytoplasmic clusterin; in panel A the antibody was directed against a glycosylated epitope of clusterin β-chain, SEQ ID No2; in panel B the antibody was generated by immunization against an antigenic epitope of β-chain, SEQ ID No 3; in panel C the antibody was directed against an antigenic epitope of clusterin α-chain, SEQ ID No 4.

The expression levels of cytoplasmic clusterin are very high in aggressive and metastatic colon carcinomas.
Total protein extracts from surgical specimens of colon carcinomas have been prepared. In particular, 15 μg of total proteins have been analyzed by Western Blot. The samples have been loaded in triplicate and analyzed with the three antibodies against the cytoplasmic glycosylated isoform (epitopes SEQ ID No 2, 3, 4). FIG. 2 shows the Western Blot analysis with each of the three antibodies. As shown, a band of 40 kDa has been detected which corresponds to the molecular weight of the glycosylated clusterin isoform.

Tests of specificity have been performed during primary antibody incubation. Serial dilution of the single peptides have been added during the primary antibody incubation, in order to compete with the bond between the clusterin of the extract and the antibody. The disappearance of the Western

TABLE 1

|  | Antibody SEQ ID No 1 | Antibody SEQ ID No 2 | Antibody SEQ ID No 2 | Antibody SEQ ID No 3 | Antibody SEQ ID No 4 |
| --- | --- | --- | --- | --- | --- |
| Clusterin | 100 | 100 | 100 | 100 | 100 |
| ApoAI | <0.001 | <0.001 | <0.001 | <0.004 | <0.006 |
| ApoE | <0.001 | <0.002 | <0.008 | <0.002 | <0.003 |
| BSA | <0.009 | <0.008 | <0.01 | <0.007 | <0.01 |

Blot signal demonstrates the specificity of the binding, already assessed by the recognition of the protein with a molecular weight of 40 kDa.

FIG. 3 shows the specificity of the antibodies for the various clusterin isoforms and demonstrates the diverse isoforms expression modulation during colon tumourigenesis. In tumoural tissues (T) the isoform that controls the proliferation and is localized in the nucleus of healthy mucosa cells (S) disappears. On the other hand, the cytoplasmic isoform implicated in membrane remodelling and cellular motility increases in tumour.

This assay would give information for the prognosis of disease. In fact, the increase of cytoplasmic clusterin in patients is correlated with colon cancer aggressiveness and correlates with recurrence of metastases in the follow-up.
This investigation could give information on potential formation of recurrences or metastasis in patients.

EXAMPLE 2

ELISA Method for Qualitative and Quantitative Determination of Clusterin in Biological Fluids The quantitative determination of clusterin/ApoJ in biological fluids (blood, seminal fluid, urine, stool, pleural and ascitic effusions, liquor) according to this invention has been developed by adapting ELISA and RIA techniques for small tumours.

The ELISA method involves the use of two antibodies against glycosylated clusterin which is secreted in biological fluids and can be used for the absolute quantitative determination of even minimal variations of clusterin in biological fluids.

A significant improvement has been obtained with the homogeneous immunological dosages that do not need physical separation of the bound fraction of the antigen from the one not bound and so facilitate the automation and speed-up the screening.

The concentration of clusterin is 100±42 µg/ml, in healthy individuals.
The method presented in this invention involves a further extension to a RIA dosage that would permit the detection of clusterin in biological fluids, according to the tumour size and its aggressiveness; in fact the RIA dosage is highly sensitive and is therefore indicated to evaluate the differences between the normal levels of clusterin and those slightly increased, due to small tumours or non aggressive ones.

Materials and Methods
Standard Curve
In order to obtain a standard curve, each peptide used for the generation of each antibody was linked to BSA molecules ed immuno-absorbed on 96-well plates in scalar dilutions.
Each peptidic sequence synthesized with the solid phase technique and used for the generation of the oligoclonal antibody against secreted clusterin was then used for the standard curve.

The reference curve was made linking the unmarked peptide to a carrier molecule of known linking capability. Cationic albumin (all the COOH groups are changed in $NH_2$, PIERCE) was then used. The conjugation of the peptide to the carrier is made with carbodiimmide or glutaraldeide (a $NH_2$ of the protein is linked to a peptide molecule).

The determination of the not bound $NH_2$ groups, before and after the peptide conjugation, give the quantity of peptide molecules conjugated per carrier mole. The $NH_2$ groups are determined with a colorimetric assay.

The standard curve was obtained with increasing quantities of the carrier-peptide compound, from 0 to saturation of each antibody that was maintained constant on plate.

Reactions that have the same quantity of antibody in samples containing the protein or the free peptide will develop an intensity that can be reported on the reference curve for quantization.

The standard curve for determination of clusterin concentration in samples was then performed plating 50 µl of solution per well in TBS+0.02% BSA+0.5% Tween-20.

ELISA

The anti-clusterin antibody of this invention used to coat the plates was diluted in a coating buffer (0.05 M carbonate buffer, pH 9.6+0.1% $NaN_3$) at a concentration of 0.5 µg/ml and incubated in 96-well plates (50 µl/well), for two hours at 37° C. (or overnight at 4° C.).

After the incubation, the unbound antibody was removed by washing in TBS (Tris Buffered Saline)+0.5% Tween-20 and 200 µl of 1% BSA in coating buffer were then added in each well and incubated for 30 minutes at 37° C.

The plates were washed in TBS+0.5% Tween-20.

The serum samples from the patients were plated in three different dilutions (50 µl/well). All the experiments were performed in triplicate.

The plates were incubated for 4 hours at 37° C. (or overnight at 4° C.) and then washed in TBS+0.5% Tween-20.

A second anti-clusterin antibody was diluted 1:200 in TBS+0.1% BSA+0.05% Tween-20+2 mM $MgCl_2$; 50 µl of this solution were added in each well and then incubated for 4 hours at 37° C. The unbound antibody was removed by washing in TBS+0.5% Tween-20.

Reaction with Specific Antibodies HRP Conjugated

The plates were incubated for 1 hour at room temperature with 100 µl of anti-rabbit goat IgG conjugated with horseradish peroxidase diluted 1:10000 in 1% BSA/TBS.

After the incubation, the plates were washed and the antibody visualized by adding 100 µl/well of detection solution which was incubated for 2 hours at room temperature in the dark; the detection solution was prepared mixing 6 µl, $H_2O_2$, 360 µl tetramethybenzidine (3 mg/ml) dissolved in acetone, 5.64 ml 0.1 M citric acid and 4.36 ml 0.2 M $Na_2HPO_4$.

The reaction was stopped by adding 100 µl 5.3% $H_2SO_4$ and optical density was read at 492 nm.

Results

By the use of the ELISA method validated as described previously, the ability of detecting small quantities of glycosylated clusterin in biological fluids, increased quantities in tumoural cells, and extracellularly secreted clusterin in the intestinal lumen, as well as in blood was evaluated.

Results obtained with this assay are shown in FIG. 4: a significant increase of the protein in the culture supernatant fraction of the ex vivo isolated tumoural cells, compared to cells from healthy mucosa of the same patient is evident. The specificity of the test is given by the comparison between the protein level in normal and neoplastic cells from the same patient. The culture medium with the same exogenous nutrients has been used as standard. The assay specificity is evident by the results.

In particular, FIG. 4 shows the clusterin concentration (µg/ml) evaluated by ELISA in the culture supernatant of the ex vivo isolated cells from healthy and neoplastic colonic mucosa. The complete culture medium was used as control. The normal ($10 \times 10^7$ cells) and neoplastic ($10 \times 10^7$ cells) cells from colonic mucosa were incubated two days at 37° C. in complete medium. The culture supernatant fraction was dosed by the ELISA assay.

The aim of the diagnostic kit according to this invention is to determine the clusterin levels in biological fluids in an absolute quantitative, specific and selective way, thus permitting a timing and not invasive diagnosis of tumours.

Specifically for colorectal cancer, the increase of glycosylated clusterin expression in the cytoplasm correlates with the tumour aggressiveness and metastatic potential. Therefore this kit can be also used for the prediction of stage and grade of the malignant disease.

Bibliography

Aronow B J, Lund D S, Brown T L, Harmony J A K and Witte D P. (1993). Proc. Natl. Acad. Sci. USA 90, 725-729.

Bettuzzi S, Scorcioni F, Astancolle S, Davalli P, Scaltriti M and Corti A. (2002). Oncogene 21, 4328-4334.

Burkey B F, DeSilva H V and Harmony J A. (1991). J. Lipid Res., 32, 1039-1048.

Fratelli M, Galli G, Minto M and Pasinetti G M. (1996). Biochim. Biophys. Acta 1311, 71-76.

Ho S M, Leav I, Ghatak 5, Merk F, Jagannathan V S and Mallery K. (1998). Am. J. Pathol., 153, 131-139.

Humphreys D T, Carver J A, Easterbroock-Smith S B and Wilson M R. (1999). J. Biol. Chem., 274, 6875-6881.

Lakins J, Bennett S A, Chen J H, Arnold J M, Morrissey C, Wong P, O'Sullivan J and Tenniswood M. (1998). J. Biol. Chem., 273, 27887-27895.

Leskov K S, Klokov D Y, Li J, Kinsella T J and Boothman D A. (2003). J. Biol. Chem., 278, 11590-11600.

Morrissey C, Lakins J, Moquin A, Hussain M, Tenniswood. (2001). J. Biochem. Biophys. Metods, 48, 13-21.

Murphy B F, Kirszbaum L, Walker I D and D'Apice A J. (1988). J. Clin. Invest., 81, 1858-1864.

O'Sullivan J, Whyte L. Drake J and Tenniswood M. (2003). Cell Death Differ., 10, 914-927.

Pucci S, Bonanno E, Pichiorri F, Angeloni C. Spagnoli L. (2004). Oncogene, advance on line publication, 1-7.

Redondo M, Villar E, Torres-Munoz J, Tellez T, Morell M and Petito C K. (2000). Am. J. Pathol., 157, 393-399.

Wong P. Pineault J, Lakins J. Taillefer D, Leger J, Wang C and Tenniswood M. (1993). J. Biol. Chem., 268, 5021-5031.

Zhou W, Janulis L, Park II and Lee C. (2002). Life Sci., 72.

Domanda di brevetto greco, No GR20020100196.

---

The invention claimed is:

1. Isolated oligoclonal antibodies able to recognize and bind the antigenic epitope of at least one glycosylated cytoplasmic or non glycosylated nuclear isoform of human clusterin in a selective and specific way,
wherein the antigenic epitope of the non glycosylated nuclear isoform is selected from the antigenic epitope consisting of SEQ ID NO: 1 (QFNWVSRLANLTQGEDQK) or the antigenic epitope consisting of non glycosylated SEQ ID NO: 2 (TKLKELPGVCNETMMALWEE), and
wherein the antigenic epitope of the glycosylated cytoplasmic isoform is selected from the antigenic epitope consisting of SEQ ID NO: 2 (TKLKELPGVCNETMMALWEE) glycosylated at its N residue, the antigenic epitope consisting of SEQ ID NO: 3 (TNEERKTLLSNLEEAK), or the antigenic epitope consisting of SEQ ID NO: 4 (METVAEKALQEYRKK), and
wherein said epitope is immunogenic.

2. Oligoclonal antibodies according to claim 1, wherein the antibodies are tagged.

3. Oligoclonal antibodies according to claim 2, wherein the antibodies are tagged with a fluorochrome, a radioactive isotope, an enzyme, biotin or a chemiluminescent substance.

4. Oligoclonal antibodies according to claim 3, wherein the fluorochrome is selected form the group consisting of fluorescein, ficoeritrine, rhodamine, texas red, and cumarine.

5. Oligoclonal antibodies according to claim 3, wherein the radioactive isotope is $^{14}C$ or $^{3}H$.

6. Oligoclonal antibodies according to claim 3, wherein the chemiluminescent substance is luciferin.

7. Oligoclonal antibodies according to claim 3, wherein the enzyme is selected from the group consisting of horseradish peroxidase (HRP) or alkaline phosphatase.

8. Isolated immunogenic antigenic epitopes of at least one human clusterin isoform selected from the antigenic epitope consisting of SEQ ID NO: 1 (QFNWVSRLANLTQGEDQK); the antigenic epitope consisting of SEQ ID NO: 2 (TKLKELPGVCNETMMALWEE); the antigenic epitope consisting of SEQ ID NO: 3 (TNEERKTLLSNLEEAK); or the antigenic epitope consisting of SEQ ID NO: 4 (METVAEKALQEYRKK).

9. A method for the preparation of the isolated oligoclonal antibodies, as defined in claim 1, which comprises the following steps:

solid phase synthesis of at least one of the antigenic epitopes of at least one human clusterin isoform selected from the antigenic epitope consisting of SEQ ID NO: 1 (QFNWVSRLANLTQGEDQK); the antigenic epitope consisting of SEQ ID NO: 2 (TKLKELPGVCNETMMALWEE), the antigenic epitope consisting of SEQ ID NO: 3 (TNEERKTLLSNLEEAK); or the antigenic epitope consisting of SEQ ID NO: 4 (METVAEKALQEYRKK);
conjugation of at least one of the antigenic epitopes wherein a proteic carrier in order to make the epitope immunogenic;
animal immunization with said immunogenic epitope in complete Freund adjuvant; and
serum withdrawal from the immunized animal and purification of the oligoclonal antibodies.

10. A method according to claim 9, wherein the proteic carrier is the bovine serum albumin.

11. A method according to claim 9, wherein the animal is rabbit.

12. An immunological method for detection of the clusterin levels in biological samples which comprises the following steps:
protein extraction from this biological sample;
specific incubation of the proteic extract with at least one of the isolated oligoclonal antibodies described in claim 1, in order to obtain an antigen antibody complex; and
qualitative and quantitative revelation of the antigen antibody complex.

13. An immunological method according to claim 12 wherein the biological sample is a tumor sample.

14. An immunological method according to claim 12, wherein the biological sample is selected from the group consisting of blood, stool, seminal fluid, pleural fluid, ascitic fluid, urine, and liquor.

15. An immunological method according to claim 13 wherein the tumor is selected from the group consisting of colorectal, breast, prostate, testis, ovarian, central nervous system and haemolymphopoietic system.

16. An immunological method according to claim 12, wherein the detection of step c) is done by using one of the following techniques: ELISA, Western Blot, RIA, immunohistochemistry.

17. Diagnostic kit for diagnosis of tumors and prediction of their malignancy grade which comprises at least one of the oligoclonal antibodies as defined in claim 1.

* * * * *

SEQUENCE LISTING

```
<160> NUMBER OF SEQ ID NOS: 4

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      antigenic epitope of the not glycosilated nuclear isoform of
      clusterin

<400> SEQUENCE: 1

Gln Phe Asn Trp Val Ser Arg Leu Ala Asn Leu Thr Gln Gly Glu Asp
1               5                   10                  15

Gln Lys

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      antigenic epitope of the not glycosilated nuclear isoform of
      clusterin

<400> SEQUENCE: 2

Thr Lys Leu Lys Glu Leu Pro Gly Val Cys Asn Glu Thr Met Met Ala
1               5                   10                  15

Leu Trp Glu Glu
            20

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      antigenic epitope of the glycosilated cytoplasmatic isoform of
      clusterin

<400> SEQUENCE: 3

Thr Asn Glu Glu Arg Lys Thr Leu Leu Ser Asn Leu Glu Glu Ala Lys
1               5                   10                  15
```

```
<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      antigenic epitope of the glycosilated cytoplasmatic isoform of
      clusterin

<400> SEQUENCE: 4

Met Glu Thr Val Ala Glu Lys Ala Leu Gln Glu Tyr Arg Lys Lys
1               5                   10                  15
```